United States Patent [19]

Caulin et al.

[11] 4,151,276

[45] Apr. 24, 1979

[54] METHOD OF SUPPRESSING GASTRIC ACID SECRETION BY THE ORAL ADMINISTRATION OF CALCITONIN

[75] Inventors: Francine B. Caulin, Saint Mande, France; James W. Bastian, Park Forest, Ill.

[73] Assignee: Armour Pharmaceutical Company, Scottsdale, Ariz.

[21] Appl. No.: 576,752

[22] Filed: May 12, 1975

[51] Int. Cl.$^2$ .............................................. A61K 35/46
[52] U.S. Cl. ................................................... 424/111
[58] Field of Search ................................ 424/112, 111

[56] References Cited

U.S. PATENT DOCUMENTS 3,826,824   7/1974   Doepfner .............................. 424/112

Primary Examiner—Frederick E. Waddell
Attorney, Agent, or Firm—Richard R. Mybeck

[57] ABSTRACT

A method of obtaining suppression of gastric acid secretion in a mammalian host by the oral administration of calcitonin to the host mammal, including man, to obtain the suppression of gastric acid secretion therein. The method is useful in the treatment of mammals having grastric or duodenal ulcers or other conditions which benefit from the suppression of gastric acidity.

8 Claims, No Drawings

METHOD OF SUPPRESSING GASTRIC ACID SECRETION BY THE ORAL ADMINISTRATION OF CALCITONIN

DESCRIPTION OF INVENTION

The present invention relates to a method of suppressing gastric acid secretion in a mammalian host by the oral administration of calcitonin to said host. The method is especially useful in the treatment of gastric and duodenal ulcers and the like and in those surgical procedures involving the stomach in which suppression of gastric acid secretion is desirable.

It is well appreciated that the treatment of gastric or duodenal ulcers is often facilitated by agents and techniques which are effective to suppress the secretion of gastric acid or which tend to neutralize the acidity of gastric secretions. Accordingly, current therapy for gastrointestinal ulcers often utilizes orally administered antacid preparations to reduce gastric acidity. Anti-cholinergic and othe types of antispasmodic drugs are also commonly employed for the purpose of suppressing the secretion of gastric acid.

It is also well-known that these therapies are not unequivocally useful because they are often inadequate to effectively neutralize all of the gastric acid to a sufficient degree or for a sufficient period of time; or they are insufficiently effective in suppressing secretion of gastric acid; or they are inconvenient, and sometimes painful, to use (e.g., the hourly administration of antacids to ulcer patients who must tolerate the presence of and suffer with a naso-gastric tube); or they are accompanied by undesirable, sometimes intolerable, side effects such as blurred vision and the like.

At the present time, we are aware of no drugs which, following oral administration, will act to suppress gastric acid secretion by a direct local action in the stomach.

Calcitonin, when administered systemically (i.e., parenterally), has been shown to have a marked ability to suppress secretion of gastric acid. See: Hesch et al, Horm. Metab. Res. 3:140 (1971). This finding was later confirmed by many other investigative groups. See: Bates et al, Horm. Metab. Res. 6:332-33 (1974); Becker et al, Amer. J. Physiol. 225(2):277-80 (1973); Bieberdorf et al, Gastroenterology 66:343-46 (1974); Bobalik et al, Proc. Soc. Exp. Biol. Med. 147:284-88 (1974); Henrichs et al, Acta Endocr. (KBH), Vol. 75, Suppl. 184:170 (1974); Konturek et al, Digestive Diseases 19(3):235-41 (1974); Nordgren et al, Scand, J. Gastroent. 9:103-09 (1974); and Orimo et al, Internat. Symp. Clin. Aspects of Metabolic Bone Disease, June 26-29 (1972), Henry Ford Hospital, Detroit, Michigan. It is demonstrable in humans as well as in a variety of lower mammalian species. See: Henrichs et al, Acta Endocr. (KBH), Vol. 75, Suppl. 184:170 (1974); Barlet et al, J. Endocr. 63:407-08 (1974); Barlet et al, Horm. Metab. Res. 6:517-521 (1974); Bobalik et al, Proc. Soc. Exp. Biol. Med. 147:284-88 (1974); and Konturek et al, Digestive Diseases 19(3):235-41 (1974). These studies also established that systemically administered calcitonin is able to suppress secretion of gastric acid to a greater extent than is usually achievable with other pharmaceutical agents available at this time. Indeed, in some situations, gastric acid secretion is essentially completely stopped by parenteral calcitonin administration. See: Becker et al, Amer. J. Surg. 127:71-75 (1974); Hesch et al, Endocrinology (1971), Proc. Third Internat. Symp., London, July 19-22, 1971 (William Heinemann Medical Books, Ltd., 1972) p. 265; and Orimo et al, Igaku No Ayumi 80(13):808-09 (1972). It should be noted that parenteral administration, e.g., intramuscular, intravenous, and subcutaneous injections, result always in the systemic distribution of calcitonin. Therefore, throughout this discussion the term "systemic administration" means the systemic distribution of a parenterally administered drug.

The ability of systemically administered calcitonin to inhibit gastric acid secretion has been shown to involve probable actions at two different points in the secretory mechanism. First, there is reason to believe that calcitonin acts directly to inhibit the acid secreting parietal cells of the gastric mucosa. Secondly, evidence also suggests that calcitonin, at least under some circumstances, acts to inhibit secretion of the hormone gastrin from the gastric antrum into the blood. Since blood-borne gastrin is a strong stimulus acting on the parietal cells to evoke acid secretion, an inhibiting effect of calcitonin on gastrin secretion would indirectly bring about a decrease in gastric acid secretion.

Based on the established ability of systemically administered calcitonin to inhibit gastric acid secretion, various experimenters have attempted to prevent the development of experimentally induced gastric or duodenal ulcers in animals. See: Barlet et al, J. Endocr. 63:407-08 (1974); Bates et al, Horm. Metab. Res. 6:332-33 (1974); Doepfner, W., Internat. Symp. Clinical Aspects of Metabolic Bone Disease, June 26-29, 1972, Henry Ford Hospital, Detroit, Michigan; Konturek et al, Digestive Diseases 19(3):235-41 (1974); Matsumoto et al, Igaku No Ayumi 83(12):733-34 (1972); Noda et al, Endocrinol. Japan. 23(1):89-90 (1973); and Orimo et al, Igaku No Ayumi 82(9):579-80 (1972). All such reports have shown positive results and have led to the speculation that systemically administered calcitonin may be therapeutically useful in the treatment of gastric or duodenal ulcers in man. U.S. Pat. No. 3,826,824 concerns the use of calcitonin (administered systemically) for the treatment of gastric and duodenal ulcers.

The phenomenon of suppression of gastric acid secretion has been demonstrated with parenteral administration of salmon calcitonin (see: Bobalik et al, Proc. Soc. Exp. Biol. Med. 147:284-88, 1974), porcine calcitonin (see: Orimo et al, Internat. Symp. Clin. Aspects of Metabolic Bone Disease, June 26-29, 1972, Henry Ford Hospital, Detroit, Michigan; Excerpta Medico, Amsterdam, 1973, pp. 648-52), human calcitonin (see: Bobalik et al, Proc. Soc. Exp. Biol. Med. 147:284-88, 1974), ane eel calcitonin (see: Orimo et al, Clin. Aspects of Metabolic Bone Disease. Proc. Internat. Symp. Clin. Aspects of Metabolic Bone Disease, Henry Ford Hospital, Detroit, Michigan, June 26-29, 1972 (Excerpta Medica, Amsterdam, 1973, pp. 648-52).

Systemic dose levels of calcitonin needed for suppression of gastric acid secretion in animals or man are such that the usual effects of the hormone on bone occur simultaneously. It is not considered possible to reduce the systemic dose of calcitonin to a level at which the gastric acid effect occurs in the absence of the effects on bone. Indeed, the threshold dose for the bone effects is generally considered below the threshold dose needed for inhibition of gastric secretion. The systemic use of calcitonin can also bring about inhibition of pancreatic secretion (see: Schmidt et al, Deutsche Medieinische Wochenschrift 96(45):1773-75, 1971), inhibition of gall bladder contraction (see: Winkler et al, Dtsch. Med.

Wschr. 98(18):957-59, 1973), inhibition of contraction of the lower esophageal sphincter (see: Waldeck et al, Dtsch. Med. Wschr. 98(21):1059-63, 1973), as well as effects on the renal excretion of sodium, calcium, phosphorous and other ions (see: Aldred et al, Proc. Soc. Exp. Biol. Med. 134 1175, 1970).

Thus, the systemic use of calcitonin for inhibition of gastric acid secretion does not satisfy medical need because it is accompanied by the unwanted side effects on other physiologic mechanisms.

The present invention is predicated upon our discovery that calcitonin, administered orally to mammals, including man, will allow the desired regulation of gastric secretions but will not cause the other physiologic actions of calcitonin, which in this therapy are unwanted, to occur.

As will hereafter appear, experiments in animals and man show that calcitonin prepared and administered in accordance with this invention, will effectively suppress gastric acid secretion. Thus, we have discovered a way to utilize the important ability of calcitonin to suppress gastric acid secretion while at the same time avoiding, for all practical purposes, any systemic effects of the hormone (i.e., the unwanted side effects on bone, the pancreas, gall bladder, kidney, etc.). Additionally, the oral administration of calcitonin is more convenient for the patient than is parenteral injection (subcutaneous, intramuscular, intravenous).

Further, the data hereinafter presented will show that not only does the intragastric administration of calcitonin suppress gastric acid secretion in animals, including man, it also prevents the formation of gastric and duodenal ulcers in experimental animal models.

While the mechanism of the present invention is not fully understood, we believe that the inhibiting effect of intragastric calcitonin may be due to a direct effect on the parietal cells or the inhibition of the production or release of antral gastrin or both simultaneously.

From the foregoing, it is apparent that a great need exists for preparations and methods for effectively suppressing gastric acid secretion in mammals while avoiding the inadequacies or unwanted side effects and cumbersome auxiliary appliances attendant the prior art methods.

Accordingly, it is a prime object of this present invention to provide improved methods of obtaining the suppression of gastric acid secretions in mammals, including man, while avoiding untoward side effects.

Another object of the present invention is to provide improved methods of administering calcitonin locally to mammals, including man, wherein the gastric acid suppression properties are obtained while the physiological effects associated with systemic delivery are substantially completely eliminated.

Still a further object of the present invention is to provide an improved and convenient method of delivering calcitonin to a host mammal, including man, which obtains the beneficial local action thereof without requiring naso-gastric tubes or other uncomfortable appliances to be attached in or to the host.

These and still further objects as may hereinafter appear are fulfilled by the present invention in a remarkably unexpected and totally unobvious manner as will be readily discerned from the following detailed description of exemplary embodiments thereof.

"Calcitonin" as used herein defines those peptides having an extended amino acid chain (usually 32) and obtained from thyroid tissue of mammals or the ultimobranchial glands of fish and fowl or synthetically. Calcitonin is known to have certain characteristic actions on bone, kidney and the gastro intestinal tract, the most notable effect being the inhibition of bone resorption.

Porcine calcitonin can be obtained from mammalian thyroid tissue by any of the known procedures such as that described in Arnaud et al, Excerpta Medica, 157, P. 7 (1968).

Fish calcitonin, that is, salmon, eel, and trout, likewise can be obtained by any known procedure from ultimobranchial tissue such as that described in Copp et al, Proceedings, Third Parathyroid Conference, 3, p. 24 (1968).

Synthetic calcitonin likewise may be prepared by any known procedure such as those described in Guttmann et al, Helvetica Chemica Acta, 52, p. 1789 (1969) or Rittel et al, Ibid, 51, p. 924 (1968) or Rivaille et al, Helvetica Chemica Acta, 55, p. 1671 (1972).

Calcitonin prepared by any of the foregoing procedures, or by other suitable procedures, may be used as the base material or converted to a non-toxic acid addition salt (e.g., acetate or other) as hereinafter described and may be mixed with calcitonins of other species and still provide a desirable active ingredient for practice of this invention. All of the various active ingredients are herein identified as "calcitonin."

Calcitonin of this invention may be employed as a free base or in the form of a non-toxic pharmaceutically acceptable salt. Thus, for example, organic and inorganic acid addition salts may be employed, such as the salts of hydrochloric, sulfuric, phosphoric, citric, acetic, lactic, formic, tartaric, sulfamic, succinic, maleic, ethanedisulfonic, hydrobromic, benzoic and similar non-toxic acids. The salts may be prepared by reacting calcitonin with a slight (not over 5%) excess of acid in a suitable solvent, such as methanol, water, or a mixture thereof. The mixture is heated gently to effect solution, and the solvent is removed therefrom.

Calcitonin or a salt thereof, according to this invention, is administered in therapeutically effective amounts to animals, including man. Dosages of about 0.05 milligram to 10 milligrams of calcitonin are preferred for a regimen of 3-8 hour intervals for administration. The foregoing and other dosage levels herein are based on the content of the acetic acid salt.

In the preferred embodiments of the invention, calcitonin or a salt thereof is administered in a pharmaceutical composition which includes calcitonin and a pharmaceutical carrier. The carrier is a non-toxic pharmaceutical grade substance which may be either solid or liquid. Suitable solid carriers include lactose, starch, sucrose, mannitol, sorbitol, albumin, cellulose powder, talc, stearic acid, gelatin, agar, pectin, acacia and the like. Suitable liquid carriers include glycols, polyglycols, peanut oil, olive oil, sesame oil, corn oil, alcohols, water, albumin solution, aqueous gelatin, and the like.

The composition preferably is provided in unit dosage form for accuracy and convenience in oral administration. Dosage units suitable for oral administration include those employing solid carriers such as tablets, filled capsules, packets and the like. The amount of solid carrier per dosage unit may vary widely, preferably from about 10 milligrams to 5 grams.

The calcitonins and their salts may be compounded with semi-solid and liquid carriers in solutions, suspensions, emulsions, and soft gelatin capsules, for example.

The foregoing dosage forms are prepared by conventional procedures of mixing, granulating, compressing, suspending and/or dissolving, as is suitable to prepare the desired dosage form.

The gastric acid suppression in the host animal, including man, to whom such administration is desired, is readily obtained by orally administering to the host calcitonin or a pharmaceutically acceptable acid addition salt thereof in an amount sufficient to suppress the gastric acid secretion.

The compound preferably is administered at the dosage level described above and preferably in a pharmaceutical carrier. The dosage level and frequency of administration may vary from patient to patient, attention being given to the normal gastric acid secretion flow rate, the case history, the reaction of the subject, and the like.

The daily dosage can be administered in three or more parts and the administration is most conveniently accomplished by means of a tablet containing one of the active compounds and a pharmaceutical carrier.

Especially good suppression of gastric acid is obtained in the animal organism when calcitonin, selected from a group of natural calcitonins obtained from salmon, eel, porcine, human or chicken, the synthetic counterparts or analogs of the natural calcitonins, mixtures of natural and synthetic calcitonins, and the non-toxic acid addition salts thereof, is administered to the animal.

We find that the oral administration of calcitonin results in little or no systemic absorption of calcitonin. It is believed that this results from (a) a hydrolysis of calcitonin to inactive fragments by proteolytic enzymes in the digestive tract, especially in the small intestine, and (b) orally administered calcitonin apparently does not penetrate the mucosa of the gastrointestinal tract sufficiently to reach the sites from which it would be absorbed into the blood. In any event, the oral administration of calcitonin is observed to result in so significant systemic action. Thus, the oral dosage forms of the present invention permit the local suppression of gastric acidity while, at the same time, they avoid the systemic absorption of the administered calcitonin.

To further aid in the understanding of the present invention, but not by way of limitation, the following examples are presented:

EXAMPLE I

INHIBITION OF RESTRAINT-INDUCED GASTRIC ULCERATION IN RATS WITH ORAL AND INJECTED CALCITONIN, AND DEMONSTRATION OF LACK OF SYSTEMIC ACTION OF ORALLY ADMINISTERED CALCITONIN

After a light ether anesthesia, twenty-nine rats (140–210 gms., both sexes) were put dorsally on a board for five hours with the legs and tail extended by a string attached to nails. When the rats had recovered from anesthesia, they received by gastric tube, beginning at the time of the restraint period, 8.2 MRC units of porcine calcitonin dissolved in 0.25 ml of 0.01 M acetic acid. The same treatment was repeated twice more at intervals of 1 hour 24 minutes. A second group of thirteen rats received, at the same times and in the same volume of acid, 5 MRC units of porcine calcitonin by subcutaneous injection. A third group of twenty-four control rats received, at the same three time periods, by gastric tube, 0.25 ml of 0.01 M acetic acid. Five hours after the first dose of porcine calcitonin, blood samples were collected by cardiac puncture for plasma calcium determination by atomic absorption spectrophotometry, and the animals were killed by ether anesthesia. Ulcerated areas of the stomachs were measured under a magnifying glass.

As shown on Table I, porcine calcitonin given by subcutaneous injection significantly decreased the ulcerated area of the stomach in restrained rats. Porcine calcitonin given by gastric tube also significantly prevented the development of restraint-induced gastric ulcers. Ser-m calcium was lowered by porcine calcitonin administered subcutaneously but was unaffected by calcitonin given by gastric tube, thus showing the absence of significant systemic action of intragastrically administered calcitonin.

TABLE I

| Porcine Calcitonin Treated Rats | | | | Control Rats | |
|---|---|---|---|---|---|
| Gastric Tube | | S.C. Injections | | | |
| Ulcer* Area | Plasma Ca** | Ulcer* Area | Plasma Ca** | Ulcer* Area | Plasma Ca** |
| 8.2 ± 1.4 | 9.3 ± 0.1 | 2.7 ± 1.0 | 7.3 ± 0.1 | 24.2 ± 3.7 | 9.4 ± 0.1 |
| P <0.001 | N.S. | P <0.001 | P <0.001 | | |

*(mm$^2$);
**(mg/100 ml of plasma)
The statistical significance of the results was calculated by the Student's Test (treated rats versus control rats).

EXAMPLE II

INHIBITION OF GASTRIC ACID SECRETION IN PYLORUS-LIGATED RATS WITH ORAL CALCITONIN AND INJECTED CALCITONIN, AND DEMONSTRATION OF LACK OF SYSTEMIC ACTION OF ORALLY ADMINISTERED CALCITONIN

Twenty-four pylorus-ligated rats (150–170 gms.) were used to study the effect of porcine calcitonin on gastric HCl secretion. Each rat was weighed and the pylorus was ligated under ether anesthesia. Twelve rats received, just after pylorus ligation and one hour later, by gastric tube, 16.4 MRC units of porcine calcitonin. Five rats received by subcutaneous injection, at the same times, 5 MRC units of porcine calcitonin. Control rats received, by the same routes and at the same times, the same volume (0.25 ml) of 0.01 M acetic acid. The animals were killed two hours after pylorus ligation. The stomach contents were weighed. HCl secretion was measured by titration of 1 ml of gastric juice against 0.1 N NaOH.

As shown in Table II, porcine calcitonin given by gastric tube or by subcutaneous injection significantly decreased gastric acid secretion in comparison to the appropriate control group. Serum calcium values were significantly lowered by calcitonin given subcutaneously but not by calcitonin given orally. Thus, orally administered calcitonin is shown to be free of significant systemic action while still retaining the ability to suppress gastric acid secretion.

TABLE II

| PORCINE CALCITONIN TREATED RATS | | | | CONTROL RATS | |
|---|---|---|---|---|---|
| Gastric Tube | | S.C. Injections | | | |
| HCl* | Ca** | HCl | Ca** | HCl | Ca** |
| 101.9 ± 2.5 | 8.8 ± 0.1 | | | 123.0 ± 3.8 | 8.6 ± 0.1 |
| P <.001 | N.S. | | | | |
| | | 78.0 ± 4.2 | 6.7 ± 0.1 | 122.0 ± 5.1 | 8.8 ± 0.1 |
| | | P <0.001 | P <0.001 | | |

*µl equiv./hr./100 g body weight
**mg/100 ml plasma
The statistical significance of the results was calculated by the Student's Test (treated rats versus control rats).

EXAMPLE III

EFFECT OF ORAL CALCITONIN ON LEVELS OF TITRATABLE GASTRIC ACIDITY AND PLASMA CALCIUM IN HISTAMINE INJECTED, THYROIDECTOMIZED, PYLORUS LIGATED GUINEA PIGS

Twelve surgically thyroidectomized (TX) guinea pigs (supplemented with $T_4$) and four intact guinea pigs, fasted for thirty-six hours, were weighed and each had its pylorus ligated under light ether anesthesia. Just after recovery from anesthesia, these animals received Benadryl i.p. (0.75 mg/100 g). Four TX animals received porcine calcitonin intragastrally (20 MRC units/100 g); four TX animals received the same dose of porcine calcitonin which had been rendered inactive by oxidation with $H_2O_2$, intragastrally, and four TX and four intact guinea pigs received the same volume of vehicle for porcine calcitonin and oxidized porcine calcitonin (0.15 mg gelatin in 0.25 ml water) intragastrally. Twenty minutes later all the animals were injected intramuscularly with histamine (0.25 mg/100 g). Sixty minutes after the injection of histamine, blood was obtained by cardiac puncture under ether anesthesia. The stomach was removed and gastric juice was weighed. Gastric HCl secretion was measured by titration of 1 ml gastric juice against 0.1 M-NaOH. Table III shows that histamine-stimulated gastric HCl secretion is not statistically different in TX animals which received porcine calcitonin intragastrally from that of intact animals. The relatively low level of HCl secretion in the intact animals is attributed to the protective effect of endogenous calcitonin secretion, while it is significantly increased in TX animals supplemented with the vehicle alone or treated with inactivated porcine calcitonin. Thus, the inhibition of histamine-stimulated gastric secretion seems to be a true effect of the hormone, since the effect disappears after oxidation of porcine calcitonin with $H_2O_2$. This inhibition of gastric HCl secretion seems also to be independent of the well-known hypocalcemic effect of the hormone, since no hypocalcemia was observed in the animals (Table III).

TABLE III

The Influence of Porcine Calcitonin Given Intragastrally on Histamine-Stimulated Gastric HCl Secretion in the Thyroidectomized, Thyroxine ($T_4$) Supplemented Guinea Pig (Means ± S.E.M.)

| | Treatment | | | |
|---|---|---|---|---|
| | Intact + Vehicle. | Thyroidectomy + $T_4$ | | |
| | | Oxidized Porcine Calcitonin | Vehicle | Porcine Calcitonin |
| Plasma ca (mg/100 ml) | 9.7 ± 0.1 | 9.8 ± 0.2 | 9.9 ± 0.2 | 9.2 ± 0.2 |
| Gastric HCl (µ equiv./100 g/h) | 210 ± 7 | 341 ± 28* | 307 ± 17* | 202 ± 15 |

Statistical significance was calculated according to Student's t-test by comparing each group of thyroidectomized animals with the intact controls: *P < 0.05; al other values not significant. Four animals in each group.

EXAMPLE IV

DELAYED DEATHS WITH ORAL CALCITONIN TREATMENT IN GUINEA PIGS WITH PERFORATING GASTRIC ULCERS INDUCED BY REPEATED ADMINISTRATION OF HISTAMINE

Eighteen male guinea pigs, weighing 180–200 gms, were given food and water ad libitum throughout the experiment. Twelve were surgically thyroidectomized (TX) (with preservation of the parathyroid glands) ten days before beginning the experiment. These animals were supplemented with thyroxine ($T_4$) s.c. (50 µg/100 g/72 h), so that plasma hormonal iodine was not statistically different in TX (4.17±0.26 (S.E.M.) µg/100 ml) and in intact animals (4.29±0.12 µg/100 ml). The eighteen guinea pigs were injected i.m. with histamine (in the form of a suspension in mineral oil) three times per twenty-four hours in three equally divided doses (0.75 mg/100 g/24 hours). Benadryl was used to protect the guinea pigs against the acute non-gastric toxic effects of histamine: it was administered intraperitonally (2.25 mg/100 g/24 hours), twenty minutes before each injection of histamine. Six of the TX guinea pigs received porcine calcitonin by gastric tube (60 MRC units/100 g/24 hours), immediately after each injection of Benadryl. Six TX and six intact animals, not given porcine calcitonin received the same volume of vehicle alone (0.15 mg gelatin in 0.25 ml water). Injections were given until the animals died and the time from the first histamine injection to the moment of death was measured to the nearest hour. All the animals were autopsied and the stomachs were examined to confirm death due to perforation of a peptic ulcer with consequent peritonitis. It was found that thyroidectomy plus $T_4$ supplementation significantly (P <0.001) accelerated the development of histamine-induced peptic ulcers (the survival time of TX animals receiving $T_4$+Vehicle compared with that of intact controls was 42±3 and 109±5 h respectively). The prolonged survival of the intact animals is attributed to the protective effect of endogenous calcitonin. Time of perforation of the histamine-induced peptic ulcers in TX animals receiving $T_4$+exogenous porcine calcitonin was significantly delayed in comparison to TX animals given $T_4$ and no calcitonin treatment (103.8±8 vs 42±3 hr, respectively; $p<0.001$).

EXAMPLE V

ELEVATION OF GASTRIC pH AND INHIBITION OF RESTRAINT-INDUCED GASTRIC ULCERATION IN PIGS BY CALCITONIN GIVEN ORALLY OR INTRAMUSCULARLY, AND DEMONSTRATION OF LACK OF SYSTEMIC ACTION OF ORAL CALCITONIN

Large white Yorkshire male castrated or female pigs, aged 9-10 weeks, weighing 35-45 kg, were used. They had free access to tap water and received a pelleted diet ad libitum. Gastric ulcers were induced by the restraint technique described for rats (Bonfils et al, Rev. franc., Etudes Clin. et biol. 4: 146-150 (1959) which has already been employed for pigs (Le Bars et al, C.R. Acad. Sc. Paris 255 D: 3501-3503 (1962). The animals were fasted twenty-four hours before restraint, each pig was then hung up above the ground and firmly restrained in a wood and packing-cloth harness for twenty-four hours (Tournut et al, Revue Med. Vet. 117: 365-388 (1966). Generally two pigs were simultaneously restrained, one of them being used as a control animal. Pigs were weighed at the beginning and at the end of restraint. They were then sacrificed by electrocution. The stomach was removed and opened along the greater curvature. Gastric juice was collected and its pH measured. The stomach was examined for the number of ulcers. Ulcerated areas were measured under a magnifying-glass in each pig.

In ten restrained pigs, porcine calcitonin was given intramuscularly (4 MRC units/Kg body wt/24 hours). The total dose was dissolved in 8 ml of a 15% solution of gelatin. This volume was divided into four equal injections. Each was given at five-hour intervals, the first one being administered at the beginning of restraint. Ten restrained control pigs received in the same way the same volume of the gelatin solution alone.

In another twelve restrained pigs, porcine calcitonin was given by gastric intubation. Each pig received four equal doses of porcine calcitonin (10 MRC units/Kg body weight/administration). Each dose was dissolved in 10 ml of a 15% solution of gelatin. The first dose was given at the beginning of restraint. The three other doses were then given at five-hour intervals. Eight restrained control pigs received in the same way the same dose of porcine calcitonin oxidized with $H_2O_2$; thus devoiding it of any hypocalcemic effect. The influences of varying doses of porcine calcitonin and time of the first administration were also tested in seven additional restrained pigs. The results are shown in Tables IV, V and VI.

Among the eighteen pigs restrained during twenty-four hours which did not receive porcine calcitonin, seventeen of them developed ulcerative lesions in the glandular area of the stomach. The shape and size of these ulcers varied with each animal. In 90% of the cases, lesions were multiple.

The main lesion seemed to be a slough, separation of which left ulcer. Vascular lesions in the form of "capillary pits" were common.

Hyperkeratosis (characterized by a yellow color) of the esophageal area of the stomach was observed in 60% of the animals. Ninety-five percent of restrained pigs presented fatty infiltration of the liver. Sex did not have any significant effect on the development of these lesions.

Porcine Calcitonin given intramuscularly (4 MRC units/kg body weight/24 hours) had a significant inhibiting effect on restraint-induced gastric ulcers in all of the ten pigs (Table IV). In three pigs, when the first injection (1 MRC unit/kg body weight) of porcine calcitonin was not given before the sixth hour after the initiation of restraint, no preventive effect was observed.

In twelve restrained pigs, porcine calcitonin given intragastrally (40 MRC units/kg body weight/24 hours) inhibited significantly the development of gastric ulcers. (Table IV). This inhibition was not observed in four pigs which received only 0.5, 1, 2 or 5 MRC units/kg body weight/24 hours, respectively, nor was it observed in the eight control pigs treated with oxidized porcine calcitonin.

Porcine calcitonin given intramuscularly induced a significant hypocalcemia in restrained pigs. No significant change in plasma calcium was observed when porcine calcitonin was given by gastric tubing (Table VI).

The pH of the gastric juice from restrained pigs which received porcine calcitonin intramuscularly or intragastrally was significantly higher than in control animals at the time of slaughtering (Table V).

TABLE IV

PREVENTION OF RESTRAINT-INDUCED GASTRIC ULCER BY PORCINE CALCITONIN GIVEN INTRAMUSCULARLY OR INTRAGASTRALLY IN PIGS $$(\bar{x} \pm \frac{\sigma}{\sqrt{N}})$$

| | Porcine Calcitonin Given Intramuscularly (4 MRC units/kg b.w./24 hours) | | Porcine Calcitonin Given Intragastrally (40 MRC units/kg b.w./24 hours) | |
|---|---|---|---|---|
| | Control | Porcine Calcitonin | Oxidized Porcine Calcitonin | Porcine Calcitonin |
| Number of Pigs | 10 | 10 | 8 | 12 |
| Number of Animals Which Presented Ulcers at the End of Restraint | 9 | 0 | 8 | 2 |
| Statistical | $X^2 = 9.0$ | $P < 0.005$ | $X^2 = 8.9$ | $P < 0.005$ |

TABLE IV-continued
PREVENTION OF RESTRAINT-INDUCED GASTRIC ULCER BY PORCINE CALCITONIN GIVEN INTRAMUSCULARLY OR INTRAGASTRALLY IN PIGS $$(\bar{x} \pm \frac{\sigma}{\sqrt{N}})$$

|  | Porcine Calcitonin Given Intramuscularly (4 MRC units/kg b.w./24 hours) | | Porcine Calcitonin Given Intragastrally (40 MRC units/kg b.w./24 hours) | |
| --- | --- | --- | --- | --- |
|  | Control | Porcine Calcitonin | Oxidized Porcine Calcitonin | Porcine Calcitonin |
| Significance Ulcerated Area Per Stomach (cm$^2$) | 1.80 ± 0.20 | 0 | 2.05 ± 0.35 | 0.03 ± 0.01 |
| Statistical Significance | t = 6.71 | P < 0.001 | t = 5.37 | P < 0.001 |

*The statistical significance of the results was calculated by comparing two groups of animals according to Chi-Square test or Student's t test.

TABLE V
INFLUENCE OF TREATMENT WITH PORCINE CALCITONIN ON GASTRIC JUICE pH MEASURED IN PIGS AFTER A 24 HOUR RESTRAINT $$(\bar{x} \pm \frac{\sigma}{\sqrt{N}})$$

|  | Porcine Calcitonin Intramuscularly (4 MRC units/kg b.w./24 hours) | | Porcine Calcitonin Intragastrally (40 MRC units/kg b.w./24 hours) | |
| --- | --- | --- | --- | --- |
|  | Control | Porcine Calcitonin | Control | Porcine Calcitonin |
| Number of Animals | 10 | 10 | 8 | 12 |
| Body Weight (kg) | 35.2 ± 0.9 | 36.1 ± 0.8 | 38.9 ± 1.2 | 39.4 ± 1.6 |
| Gastric Juice pH | 1.8 ± 0.2 | 3.1 ± 0.4* | 1.9 ± 0.1 | 3.0 ± 0.3* |

*P < 0.01. The statistical significance of the results was calculated by using Student's t test for comparison of each group of treated animals with its own control group.

TABLE VI
INFLUENCE OF PORCINE CALCITONIN ON PLASMA CALCIUM LEVELS IN PIGS DURING A 24 HOUR RESTRAINT PERIOD $$(\bar{x} \pm \frac{\sigma}{\sqrt{N}})$$

|  | Times (Hours) | | | |
| --- | --- | --- | --- | --- |
|  | 0 | 6 | 12 | 24 |
| P-CT Given Intramuscularly (4 MRC units/kg b.w./24 hours) | 10.2 ± 0.1 (8) | 9.4 ± 0.2 (6) | 9.0 ± 0.1** (7) | 9.2 ± 0.3* (6) |
| Solvent | 10.2 ± 0.2 (9) | 10.3 ± 0.4 (5) | 10.2 ± 0.2 (5) | 10.1 ± 0.3 (6) |
| P-CT Given Intragastrally (40 MRC units/kg b.w./24 hours) | 10.3 ± 0.1 (8) | 10.2 ± 0.1 (9) | 10.2 ± 0.4 (6) | 10.1 ± 0.5 (7) |
| Oxidized P-CT | 10.1 ± 0.2 (7) | 10.2 ± 0.1 (6) | 10.3 ± 0.3 (7) | 10.2 ± 0.1 (5) |

*P < 0.05.
**P < 0.01. The statistical significance was calculated by using Student's t test for comparison of each of the two groups of pigs which received porcine calcitonin with its own control group at the same time of sampling. ( ) number of samples.

EXAMPLE VI
ELEVATION OF GASTRIC pH WITH ORAL CALCITONIN TREATMENT IN GASTRIN STIMULATED AND UNSTIMULATED, NON-RESTRAINED PIGS

Porcine calcitonin, in one single dose of 10 MRC units/kg body weight, dissolved in 10 ml gelatin, was given by gastric tubing to eight non-restrained pigs. These pigs were previously fasted for thirty-six hours. Purified porcine gastrin was then injected (2μg/kg body weight) through an ear vein in eight animals, just before gastric intubation. Four control animals with gastrin and three without gastrin received intragastrally the same dose of the solvent for porcine calcitonin (Table VII). Pigs were sacrificed one hour later. The stomach was removed and examined for ulcers. The pH of the gastric juice was measured.

In fasting non-restrained pigs, the pH of the gastric juice was significantly increased one hour after the intragastric administration of porcine calcitonin. In such animals, intravenous injection of gastrin induced a significant drop in the pH of gastric juice. This fall was significantly inhibited by porcine calcitonin given intragastrally (Table VII).

TABLE VII

Influence Of Porcine Calcitonin Given Intragastrally (10 MRC Units/Kg B.W.) In Non-Restrained Pigs On The pH Of The Gastric Juice, Measured One Hour After Porcine Calcitonin Administration $$(\bar{x} \pm \frac{\sigma}{\sqrt{N}})$$

| Fasting Pigs | | Fasting Pigs Injected with Porcine Gastrin (2 μg/kg) | |
|---|---|---|---|
| Porcine Calcitonin | Control | Porcine Calcitonin | Control |
| 3.7 ± 0.3 | 2.8 ± 0.1 | 3.4 ± 0.5 | 1.6 ± 0.3 |
| (4) | (3) | (4) | (4) |
| $P < 0.05$ | | $P < 0.01$ | |

The statistical significance of the results was calculated by comparing two groups of animals using Student's test. ( ) number of animals.

EXAMPLE VII

ELEVATIONS OF GASTRIC pH IN HUMANS WITH ORAL CALCITONIN TREATMENT

Normal human subjects, as well as patients with varying diagnoses, were used in a study to determine the effect of orally administered porcine calcitonin on gastric pH. Porcine calcitonin was given as a single administration at a dose of 160 MRC units and was administered with 50 mgs of gelatin in a glass of water. Gastric pH measurements were made at predetermined intervals by means of a Heidelberg capsule (a capsule which is ingested orally and which is capable of telemetering gastric pH changes to external monitoring devices). As a control, pH measurements were made in five subjects not receiving treatment with calcitonin. Results are shown in Table VIII below. It is shown that the oral administration of porcine calcitonin raised intragastric pH markedly in many but not all subjects. In contrast, no comparable pH elevations occurred in any of five subjects not receiving calcitonin treatment.

TABLE VIII

| | | TIMES OF GASTRIC pH MEASUREMENT (HOURS) | | | | | | | |
|---|---|---|---|---|---|---|---|---|---|
| | | −½ | 0* | 1 | 2 | 3 | 4 | 5 | 6 |
| Controls Subjects: | (1) | 0.8 | 0.8 | 1.0 | 1.0 | 1.0 | 1.0 | 1.0 | 1.0 |
| | (2) | 1.1 | 1.1 | 1.0 | 1.0 | 1.0 | 1.0 | 0.9 | 0.9 |
| | (3) | 1.2 | 1.2 | 1.0 | 1.0 | 1.0 | 1.0 | 1.2 | 1.2 |
| | (4) | 1.6 | 1.6 | 1.6 | 1.5 | 1.5 | 1.5 | 1.4 | 1.4 |
| | (5) | 0.9 | 0.9 | 1.1 | 1.1 | 1.0 | 0.9 | 0.9 | 1.0 |
| Average: | | 1.1 | 1.1 | 1.1 | 1.1 | 1.1 | 1.1 | 1.1 | 1.1 |
| Calcitonin Treated Subjects: | (1) | 1.0 | 1.0 | 7.5 | 7.0 | 7.0 | 7.0 | 7.0 | 3.0 |
| | (2) | 1.2 | 1.2 | 6.4 | 6.6 | 6.0 | 6.0 | 6.2 | 1.8 |
| | (3) | 1.2 | 1.2 | 6.5 | 5.5 | 6.8 | 6.2 | 1.2 | 1.2 |
| | (4) | 1.6 | 1.6 | 1.2 | 6.8 | 4.5 | 1.6 | 1.5 | 1.5 |
| | (5) | 0.7 | 0.7 | 1.6 | 2.4 | 5.0 | 5.5 | 2.5 | 0.8 |
| | (6) | 1.8 | 1.8 | 6.0 | 6.0 | 6.5 | 6.5 | — | — |
| | (7) | 1.0 | 1.0 | 6.0 | 5.5 | 6.0 | 5.5 | 5.5 | — |
| | (8) | 1.1 | 1.0 | 4.0 | 6.0 | 6.0 | 6.0 | 6.0 | 1.1 |
| | (9) | 1.5 | 1.5 | 5.5 | 6.0 | 5.0 | 6.0 | — | — |
| | (10) | 1.8 | 1.8 | 5.8 | 6.0 | 6.0 | 5.5 | — | — |
| | (11) | 1.0 | 1.0 | 0.8 | 1.2 | 5.6 | 5.0 | — | — |
| | (12) | 0.8 | 0.8 | 0.7 | 5.8 | 3.8 | 0.8 | 0.8 | 0.8 |
| | (13) | 1.2 | 1.3 | 6.5 | 1.2 | 1.3 | 1.3 | 1.2 | 1.2 |
| | (14) | 1.4 | 1.4 | 1.4 | 5.0 | 4.0 | 1.8 | 1.6 | 1.5 |
| | (15) | 2.0 | 2.0 | 5.0 | 6.0 | 5.0 | 4.5 | 3.6 | 3.0 |
| | (16) | 0.8 | 0.8 | 1.2 | 4.5 | 4.5 | — | — | — |
| | (17) | 0.8 | 1.0 | 6.0 | 1.0 | 0.8 | 1.0 | 1.0 | 1.1 |
| | (18) | 1.5 | 1.6 | 1.8 | 2.3 | 1.6 | 1.6 | 1.7 | 1.6 |
| | (19) | 0.8 | 0.8 | 0.8 | 6.5 | 1.5 | 0.8 | 0.8 | 0.8 |
| | (20) | 1.6 | 1.6 | 2.0 | 1.4 | 1.8 | 1.7 | 1.7 | 1.6 |
| | (21) | 0.8 | 0.8 | 4.5 | 0.5 | 0.8 | 0.8 | 0.8 | 0.7 |
| | (22) | 1.7 | 1.7 | 1.7 | 6.5 | 2.1 | 2.1 | 2.0 | 2.1 |
| | (23) | 1.2 | 1.0 | 1.5 | 2.0 | 1.0 | 1.0 | 1.1 | 1.1 |
| | (24) | 0.8 | 0.8 | 1.5 | 0.8 | 2.0 | 0.6 | 0.8 | 0.8 |
| | (25) | 0.8 | 0.8 | 2.5 | 1.8 | 2.0 | 1.0 | 1.0 | 0.9 |
| | (26) | 1.5 | 1.4 | 1.2 | 1.0 | 1.2 | 1.2 | 1.3 | 1.2 |
| | (27) | 1.6 | 1.4 | 1.5 | 1.8 | 2.0 | 1.8 | 1.7 | 1.6 |
| | (28) | 0.8 | 0.8 | 1.2 | 2.2 | 0.8 | 1.0 | 1.0 | 1.0 |
| | (29) | 1.0 | 1.0 | 0.8 | 0.8 | 0.8 | 0.9 | 1.0 | 1.0 |
| | (30) | 2.0 | 2.0 | 2.0 | 2.1 | 2.2 | 2.2 | 2.3 | 2.3 |
| Average: | | 1.2 | 1.2 | 3.2 | 3.7 | 3.5 | 3.0 | 2.2 | 1.4 |

*Time of Calcitonin Administration in Treated Subjects

From the foregoing description and examples it is apparent that a new and useful method of suppressing gastric acid secretion has been discovered which fulfills all of the aforestated objectives in a remarkably unexpected fashion. It is of course understood that the several examples herein disclosed are for illustrative purposes only and that such alteration, modifications and applications as readily occur to the artisan confronted with this disclosure are intended within the spirit of this invention, especially as it is defined by the scope of the claims appended hereto.

What we claim is:

1. A method of suppressing gastric acid secretion in a mammalian host when the suppression of gastric acid secretion in such host is medically desirable comprising administering orally to said host an effective amount of calcitonin selected from the group consisting of calcitonin obtained from salmon, trout, eel, porcine, human or chicken, the synthetic counterparts thereof, and mixtures of any of the foregoing, or their non-toxic pharmaceutically acceptable salts sufficient to suppress gastric acid secretion in said host by local action but insufficient to produce significant systemic effects normally associated with parenteral calcitonin and administration.

2. The method of claim 1 in which calcitonin is synthetic.

3. The method of claim 1 in which said calcitonin is derived from the ultimobronchial bodies.

4. The method of claim 1 in which said calcitonin is porcine calcitonin.

5. The method of claim 3 in which said calcitonin is obtained from salmon ultimobronchial bodies.

6. The method of claim 1 in which said effective amount comprises from about 0.05 milligrams to about 10 milligrams of calcitonin (based on content of acetic acid salt equivalency) in a regimen of 3–8 hour intervals between administration.

7. The method of claim 6 in which said effective amount is disposed into a non-toxic pharmaceutical grade carrier.

8. The method of claim 7 in which said carrier is selected from the group consisting of lactose, starch, sucrose, mannitol, sorbitol, albumin, cellulose powder, talc, stearic acid, gelatin, agar, pectin, acacia, glycols, polyglycols peanut oil, olive oil, sesame oil, corn oil, alcohol, water, albumin solutions, aqueous gelatin and is administered in a dosage form selected from tablets, filled capsules, packets, solution, suspension, emulsion and soft gelatin capsules.

* * * * *